(12) United States Patent
Benjamin

(10) Patent No.: US 6,852,261 B2
(45) Date of Patent: Feb. 8, 2005

(54) SOFT TIP GUIDING CATHETER AND METHOD OF FABRICATION

(75) Inventor: Thierry Benjamin, Lynn, MA (US)

(73) Assignee: Medtronic, Inc., Minneapolis, MN (US)

(*) Notice: Subject to any disclaimer, the term of this patent is extended or adjusted under 35 U.S.C. 154(b) by 741 days.

(21) Appl. No.: 09/843,748

(22) Filed: Apr. 30, 2001

(65) Prior Publication Data

US 2001/0016702 A1 Aug. 23, 2001

Related U.S. Application Data

(62) Division of application No. 09/188,760, filed on Nov. 9, 1998, now Pat. No. 6,245,053.

(51) Int. Cl.[7] .......................... B29C 65/02; B29C 43/12

(52) U.S. Cl. ...................... 264/248; 264/249; 264/296; 264/319; 156/85; 156/86; 156/294; 156/304.2; 156/304.6

(58) Field of Search ................................ 264/248, 249, 264/296, 319; 156/85, 86, 294, 304.2, 304.6

(56) References Cited

U.S. PATENT DOCUMENTS

| 4,251,305 A | * | 2/1981 | Becker et al. ............... 156/86 |
| 4,283,447 A | | 8/1981 | Flynn |
| 4,531,943 A | | 7/1985 | Van Tassel et al. |
| 4,540,404 A | | 9/1985 | Wolvek |
| 4,551,292 A | | 11/1985 | Fletcher et al. |
| 4,563,181 A | | 1/1986 | Wijayarathna et al. |
| 4,636,272 A | * | 1/1987 | Riggs ........................ 156/158 |
| 4,863,442 A | | 9/1989 | DeMello et al. |
| 4,886,506 A | | 12/1989 | Lovgren et al. |
| 4,899,787 A | | 2/1990 | Ouchi et al. |
| 4,921,483 A | | 5/1990 | Wijay et al. |
| 4,931,037 A | | 6/1990 | Wetterman |
| 5,078,702 A | | 1/1992 | Pomeranz |
| 5,160,559 A | | 11/1992 | Scovil et al. |
| 5,178,158 A | | 1/1993 | de Toledo |
| 5,205,830 A | | 4/1993 | Dassa et al. |

(List continued on next page.)

FOREIGN PATENT DOCUMENTS

| EP | WO 89/09634 | 10/1989 |
| EP | 0850653 A2 | 1/1998 |

*Primary Examiner*—Stefan Staicovici
(74) *Attorney, Agent, or Firm*—Sterne, Kessler, Goldstein & Fox P.L.L.C.

(57) ABSTRACT

The present invention relates to medical vascular catheters adapted to be inserted into a blood vessel from an incision through the skin of a patient for introducing other devices or fluids for diagnostic or therapeutic purposes, and particularly to an improved distal soft tip or segment attachment with a relatively stiff proximal catheter shaft. A tubular sleeve is bonded through the application of pressure and heat to a distal portion of the catheter shaft and a proximal portion of the distal segment of soft distal tip bridging the attachment junction. In the preferred method, the catheter shaft distal end is aligned with the distal segment or soft tip proximal end and the sleeve is fitted over the attachment junction. A heat shrink tube is fitted over the sleeve and adjoining portions of the catheter shaft and the distal segment or distal soft tip and heat is applied. The shrinkage force of the heat shrink tube over the assembly of the tubular sleeve overlying and bridging the attachment junction and the applied heat melts and force the materials of the tubular sleeve and the catheter shaft and the distal segment or distal soft tip together to fill interstitial spaces of the attachment junction and reduces the outer diameter of the sleeve. The heat shrink tube is removed after the assembly cools and solidifies. Preferably, the catheter shaft distal end and the soft tip or intermediate segment proximal end are each formed with a like plurality of ungular cut sections that are complementary in shape to one another, whereby the ungular cut sections are aligned with and mated together along the attachment junction.

6 Claims, 4 Drawing Sheets

U.S. PATENT DOCUMENTS

| | | |
|---|---|---|
| 5,221,270 A | 6/1993 | Parker |
| 5,234,416 A | 8/1993 | Macaulay et al. |
| 5,240,537 A | 8/1993 | Bodicky |
| 5,279,596 A | 1/1994 | Castaneda et al. |
| 5,292,311 A | 3/1994 | Cope |
| 5,342,383 A | 8/1994 | Thomas |
| 5,366,442 A | 11/1994 | Wang et al. |
| 5,509,910 A | 4/1996 | Lunn |
| 5,545,149 A | 8/1996 | Brin et al. |
| 5,569,221 A | 10/1996 | Houser et al. |
| 5,653,697 A | 8/1997 | Quiachon et al. |
| 5,676,659 A | 10/1997 | McGurk |
| 5,683,370 A | 11/1997 | Luther et al. |
| 5,725,513 A | 3/1998 | Ju et al. |
| 5,733,400 A | 3/1998 | Gore et al. |
| 5,738,666 A | 4/1998 | Watson et al. |
| 5,738,742 A | 4/1998 | Stevens |
| 5,755,704 A | 5/1998 | Lunn |
| 5,811,043 A | 9/1998 | Horrigan et al. |
| 5,836,925 A | 11/1998 | Soltesz |
| 5,897,537 A | 4/1999 | Berg et al. |
| 5,906,605 A | 5/1999 | Coxum |
| 5,938,653 A | 8/1999 | Pepin |
| 5,971,975 A | 10/1999 | Mills et al. |
| 5,993,415 A | 11/1999 | O'Neil et al. |
| 6,063,318 A * | 5/2000 | Houser et al. .............. 264/248 |
| 6,238,376 B1 * | 5/2001 | Peterson .................... 604/264 |

* cited by examiner

SOFT TIP GUIDING CATHETER AND METHOD OF FABRICATION

CROSS-REFERENCE TO RELATED APPLICATIONS

This application is a division of application Ser. No. 09/188,760, filed Nov. 9, 1998, now U.S. Pat. No. 6,245,053, for SOFT TIP GUIDING CATHETER AND METHOD OF FABRICATION in the name of Thierry H. Benjamin.

FIELD OF THE INVENTION

The present invention relates to medical vascular catheters adapted to be inserted into a blood vessel from an incision through the skin of a patient for introducing other devices or fluids for diagnostic or therapeutic purposes, and particularly to an improved distal soft tip or segment attachment with a relatively stiff proximal catheter shaft.

BACKGROUND OF THE INVENTION

Catheters are tube-like medical instruments that are inserted into a body cavity organ or blood vessel for diagnostic or therapeutic reasons. Medical vascular catheters are particularly designed for insertion into the vasculature and are available for a wide variety of purposes, including diagnosis, interventional therapy, drug delivery, drainage, perfusion, and the like. Medical vascular catheters for each of these purposes can be introduced to numerous target sites within a patient's body by guiding the catheter through an incision made in the patient's skin and a blood vessel and then through the vascular system to the target site.

Medical vascular catheters generally comprise an elongated, flexible catheter tube or body with a catheter side wall enclosing a catheter lumen extending between a catheter body proximal end coupled to a relatively more rigid catheter hub to a catheter body distal end. The catheter body may be relatively straight or inherently curve or curved by insertion of a curved stiffening wire or guide wire through the catheter lumen. The catheter body and catheter side wall are typically fabricated and dimensioned to minimize the catheter body outer diameter and side wall thickness and to maximize the catheter lumen diameter while retaining sufficient side wall flexibility and strength characteristics to enable the catheter to be used for the intended medical purpose.

One of the therapeutic procedures applicable to the present invention is known as percutaneous transluminal coronary angioplasty ("PTCA"). PTCA can be used, for example, to reduce arterial build-up of cholesterol fats or atherosclerotic plaque. Catheters must have sufficient stiffness to be pushed through vessels as well as rigidity to provide a high degree of torsional control. Stiffness or rigidity in the catheter tip poses the danger of puncturing or otherwise damaging a vessel as it twists through the vascular system. It is therefore desirable for catheters to have a soft or flexible distal tip. The trend toward thin side wall catheters of less than 0.3 mm wall thickness and a softer distal tip results, however, in a substantially weaker bond between the distal soft tip and the catheter shaft.

Commonly-owned U.S. Pat. Nos. 5,509,910 issued to Lunn and 5,545,149 issued to Brin et al. describe various prior art methods of attaching distal soft tips to proximal catheter shafts and their improvements upon those methods. In the '910 and '149 patents, a composite proximal catheter shaft is employed that is formed of an outer tube or sheath, an inner liner surrounding the catheter lumen and a wire braid reinforcing layer between the outer sheath and inner liner. In both cases, a distal soft tip is attached at the distal end of the catheter shaft through the employment of an intermediate segment. The presence of wire braid and TEFLON® (polytetrafluoroethylene or PTFE) in a typical multi-layer catheter shaft compromises the bond between the catheter shaft and a distal tip segment since the materials used for the soft tip do not bond well to wire braid or to TEFLON®. Thus, the transition segment is utilized between the distal end of the catheter shaft and the distal tip segment which is comprised of materials with a high tensile strength relative to the materials comprising the soft tip. As a result, the high strength of the transition segment compensates for the compromised bonding with the multi-layer catheter shaft and yields acceptable bond strength with the distal soft tip. The use of a high tensile strength transition segment is particularly important to achieving acceptable bond strength where the catheter wall thickness is less than 0.3 mm and when the soft tip material is a low tensile strength material, such as Shore 80A Pellethane® polyurethane.

In the '910 patent, a high tensile strength transition segment, selected from a group of thermoplastic elastomers having an ultimate tensile strength of at least 45 MPa is injection molded between the pre-formed distal soft tip and the distal end of the catheter shaft. The transition segment is injected in a molten state to encapsulate the modified surface geometries of the distal catheter shaft and the proximal soft tip segment to create the improved lap joint. Furthermore, the surface geometry of both the distal end of the elongated tubular shaft and the distal tip segment are modified to reduce stress concentration and increase surface area so that the adequate bonding to the distal tip segment is achieved. The use of a high tensile strength transition segment coupled with a modified surface geometry substantially increases the tensile strength of the bond between the catheter shaft and the distal soft tip. In the preferred embodiment, a modified surface geometry on the distal end of the catheter shaft is created by removing two ungular sections on either side of the central longitudinal axis of the catheter shaft. Similarly, the surface geometry on the proximal end of the tip segment is modified by removing two ungular sections on either side of the central longitudinal axis of the tip segment. An alternative embodiment is the removal of more than two ungular sections on either or both of the distal end of the catheter shaft or the proximal end of the soft tip segment to further promote bonding.

In the '149 patent, an improved method of soft tip attachment is disclosed where lap joints are formed between a pre-formed distal soft tip and a pre-formed intermediate transition tube or segment and between the transition segment and the distal end of a reinforced proximal catheter shaft. In this case, the pre-formed parts are assembled on a mandrel and within a heat shrink tube, and the assembly is subjected to IR heating. The applied heat and the pressure of the shrinkage of the heat shrink tube causes localized melting to take place at the abutting ends of the transition segment with the distal end of the catheter shaft and the proximal end of the distal soft tip. The heat shrink tube and the mandrel are removed after the assembly is cooled and the joints have solidified.

Radio frequency (RF) energy sources have also been employed to thermally bond a pre-formed distal soft tip to a wire braid reinforced catheter shaft. The RF energy is applied to the parts assembled over a mandrel, and the heat causes the materials to fuse at the butt joint.

A problem which arises with these approaches is that the lap joints or butt joints which bond the catheter shaft, transition segment, and distal soft tip are attained through substantial pressure and/or heat which can have the adverse effects on the concentricity, stiffness, and kink resistance of the catheter shaft. In general, it is desirable to reduce the thickness of the catheter shaft side wall and the distal soft tip and any intermediate segments as much as possible to maximize the catheter lumen ID for any specified French size catheter. The thickness reduction results in less bonding surface area for the lap or butt joints and also causes the wire braid to become exposed through the thin outer sheath as the sheath material contracts into the interstitial spaces of the braid when heat is applied to form the bond. The exposed braid makes the catheter body rough or irregular at the junction and the thinning can weaken the side wall.

Thus, an improved soft tip is needed which provides adequate bond strength to the catheter shaft where the wall thickness of the catheter shaft is less than 0.3 mm and the tip material is of the requisite softness without compromising concentricity, stiffness, or kink resistance of the catheter shaft. The present invention solves this problem.

SUMMARY OF THE INVENTION

The present invention is directed to a catheter and particularly to a PTCA guiding catheter having a catheter body terminating with a distal soft tip. The catheter comprises an elongated, tubular catheter shaft having proximal and distal ends, and a flexible, non-traumatic, tubular distal soft tip having a proximal end which is bonded to the catheter shaft distal end at an attachment junction. In accordance with the present invention, the attachment junction is formed and maintained through the use of a tubular sleeve that surrounds the attachment junction and extends proximally and distally through the length of the sleeve over a distal portion of the catheter shaft and a proximal portion of the distal soft tip. The sleeve is shrunk under applied heat and force so that the sleeve material melts and adheres to the catheter body and distal tip portions and melts into the attachment junction to affect adhesion of the distal soft tip to the catheter shaft distal end. The sleeve is formed of a thin, thermoplastic material, and the melting shrinks its diameter and wall thickness so that the outer diameter of the catheter body is not substantially increased by the sleeve.

In the preferred embodiment, a modified surface geometry on the distal end of the catheter shaft is created by removing two ungular sections on either side of the central longitudinal axis of the catheter shaft. Similarly, the surface geometry on the soft tip proximal end is modified by removing two ungular sections on either side of the central longitudinal axis of the distal soft tip. An alternative embodiment involves the removal of more than two ungular sections on either or both of the catheter shaft distal end or the soft tip proximal end to effectively increase the length of the attachment junction that the melted sleeve material flows into to further reinforce the bonding of the distal soft tip with the catheter shaft distal end.

The preferred method of the present invention comprises the steps of aligning the distal soft tip proximal end with the catheter shaft distal end whereby the attachment junction is characterized by interstitial spaces caused by irregular contact of the soft tip proximal end with the catheter shaft distal end. Then, the assembled parts are adhered together at the abutting ends thereof by application of heat, e.g., RF energy, to them, thereby forming a catheter body sub-assembly. A mandrel is inserted through the catheter lumen of the catheter sub-assembly, and a tubular sleeve is fitted over a distal portion of the catheter shaft and a proximal portion of the distal soft tip such that the sleeve bridges the attachment junction. Heat and pressure are applied to the tubular sleeve. The underlying distal portion of the catheter shaft and proximal portion of the distal soft tip soften or melt, and the materials of the tubular sleeve adhere with the catheter shaft and the distal soft tip. Any interstitial spaces of the attachment junction are filled, and the outer diameter and wall thickness of the sleeve are reduced.

The step of applying heat and pressure further preferably comprises fitting a heat shrink tube over the tubular sleeve and a distal portion of the catheter shaft and the entire distal soft tip. Sufficient heat is applied to shrink the heat shrink tube which thereby applies force to the assembly of the tubular sleeve overlying the distal portion of the catheter shaft and the proximal portion of the distal soft tip bridging the attachment junction. The heat shrink tube is removed after the assembly is cooled.

The method can also be applied to the attachment of the relatively stiff proximal shaft section with an intermediate and relatively more flexible catheter segment, the attachment of successive catheter segments and the attachment of a penultimate catheter segment with a final distal segment or distal soft tip.

Advantageously, the sleeve reinforces the butt joints while not appreciably increasing the outer diameter of the catheter body at each junction where it is employed. In the specific case of wire braid reinforced catheter shafts, the sleeve covers any exposed wire braid surface. However, it will be understood that the present invention can be employed in attachment of distal soft tips to other forms of catheter shafts or to intermediate or transition segments. Moreover, the present invention can be employed to attach and/or reinforce the attachment junctions of the segments of a multiple segment catheter body.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other objects, advantages and features of the invention will become apparent from the following detailed description of the preferred embodiments of the invention, in which.

DETAILED DESCRIPTION OF THE PREFERRED EMBODIMENTS OF THE INVENTION

The present invention provides an improved construction for catheters of the type having an elongated catheter body and catheter hub at the catheter body proximal end with at least one catheter lumen extending through the catheter hub and body and to a catheter body distal end thereof. The catheter body is formed of a catheter shaft having a catheter shaft proximal end coupled to the catheter hub and of a relatively short and tubular distal soft tip coupled to the catheter shaft distal end. Such constructions are particularly useful for forming medical vascular catheters in a wide range of catheter body lengths and outer diameters. Such catheters include small diameter vascular catheters, having catheter body outside diameters of 4 mm (12 F) preferably below 2.67 mm (8 F), and frequently as small as 1 mm (3 F), and below, such as those used in neurological diagnostic and interventional procedures. Such small diameter vascular catheters will also be useful for other procedures, such as gynecological procedures, cardiac procedures, general interventional radiology procedures, and the like, for access to the small vasculature as necessary. Constructions of the present invention, however, are not limited to such small diameter catheters, and will be useful for larger diameter catheters as well, such as vascular guiding catheters and PTCA balloon catheters which may have outside diameters larger than 4 mm.

Medical vascular catheters according to the present invention will comprise a catheter body having dimensions, a particular side wall construction and a geometry selected for the intended use. The catheter body will typically have a length in the range from about 40 cm to 200 cm, usually having a length in the range from about 60 cm to 175 cm. The outside diameter of the catheter body will typically be in the range from about 0.33 mm (1 F) to 4 mm (12 F), usually being in the range from about 0.66 mm (2 F) to about 3.33 mm (10 F). The catheter body will define an inner lumen typically having a diameter in the range from about 0.1 mm to 3.6 mm, usually being in the range from about 0.3 mm to 3.0 mm, with catheters having larger outside diameters usually having larger catheter lumen diameters.

Figure 1:
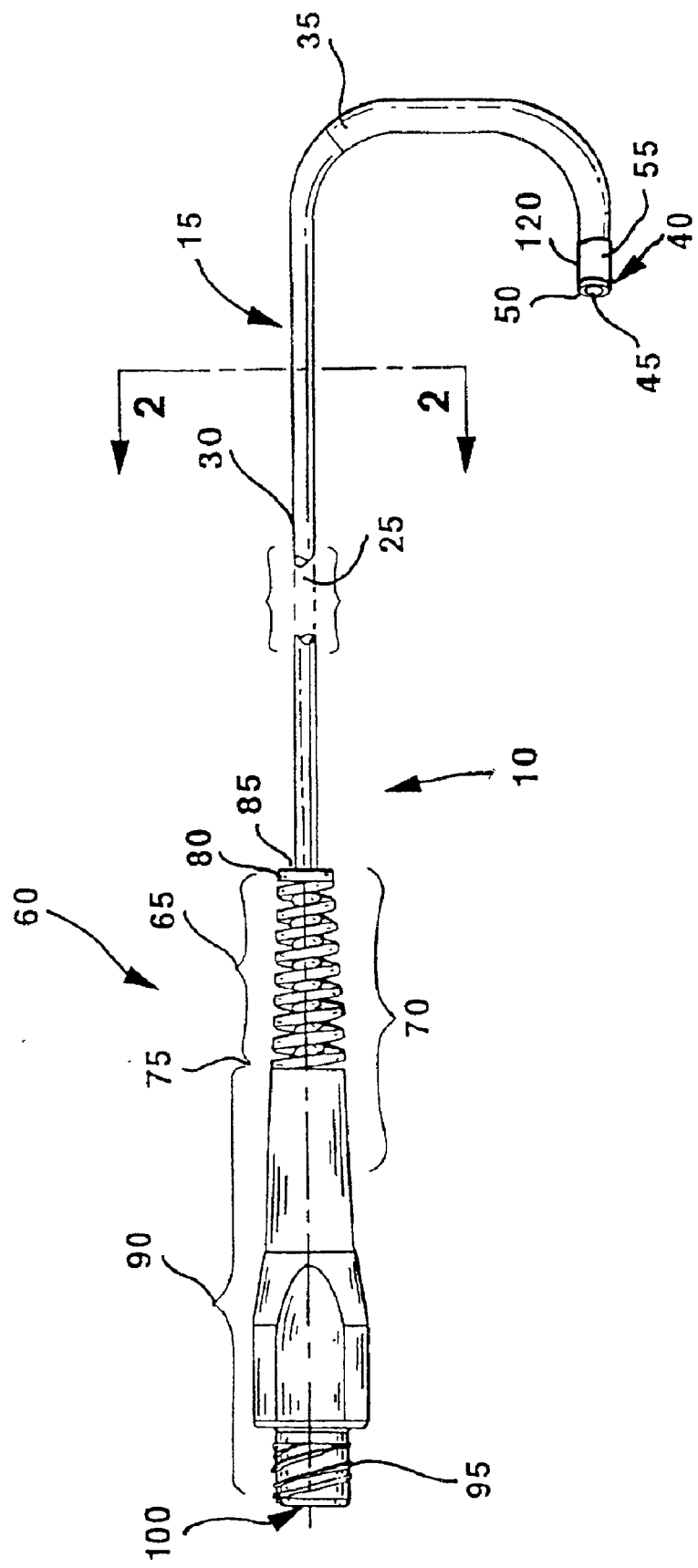
FIG. 1 is a plan view of an exemplary medical vascular catheter constructed with a the distal soft tip incorporating an overlying sleeve in accordance with a preferred embodiment of the invention.

FIG. 1 is a plan view of an exemplary medical vascular catheter 10 constructed with a unitary catheter hub and strain relief 60 of the type disclosed in the above-referenced '682 and '241 patent applications, for example. In this illustrated embodiment, the unitary catheter hub and strain relief 60 is injection molded as a single piece over a catheter hub/body junction 70 and includes a proximal hub portion 90 and a strain relief coil 65. The hub portion 90 surrounds and defines a hub lumen 100 extending to the catheter body lumen 25 of the catheter body 15. The proximal hub portion 90 is integrally connected to the proximal strain relief coil end 75 of the strain relief coil 65. The strain relief coil 65 is a continuous coil of constant or variable pitch having coil turns that decrease in diameter from the proximal strain relief coil end 75 to the distal strain relief coil end 80. The turns of the strain relief coil 65 are preferably molded over a distal portion of exterior surface of the catheter body 15 in the catheter hub body junction 70 and adhered in a spiral pattern to the exterior surface of the catheter body. In this manner, a strain relief coil lumen 85 is effectively formed because the distal portion of exterior surface of the catheter body 15 extending the length of the catheter hub/body junction 70 functions as a mandrel. This construction is merely exemplary, and it will be understood that the present invention can also be implemented in a catheter employing a catheter hub of any of the known configurations.

The catheter body 15 will usually be straight along all or most of its length, that is it will assume a straight or linear configuration, when free from external bending forces. The catheter body 15, however, will be highly flexible so that it may be able to pass through the tortuous twists and turns of a patient's vasculature. In some cases, the catheter body 15 may have a shaped distal end portion including curves and bends which are selected to facilitate introduction and placement of the catheter 10 (usually over a separate guide wire) in the vascular system. A particular geometry of curves and/or bends may be selected to accommodate the intended use of the catheter 10.

In a broad overview of the present invention, the catheter body 15 comprises at least a proximal catheter shaft 30 and a distal soft tip 40, and the catheter shaft may be constructed in any acceptable manner to provide desired characteristics. However, the catheter body 15 can also comprise at least one and at times more than one transition segment, wherein each of the transition segments has a different construction resulting in different mechanical properties. For example, the catheter shaft 30 can be constructed to have flexibility that increases distally. FIG. 1 is intended to encompass any such construction and to illustrate the completed catheter in accordance with the method of the present invention.

In FIG. 1, the catheter shaft 30 extends from the unitary catheter hub and strain relief 60 to a location spaced within 1 cm of the catheter body distal end 50, usually from 2 mm to 6 mm of the catheter body distal end 50 and preferably 3.5 mm +/− 0.50 mm. The proximal catheter shaft 30 is preferably reinforced in catheter shaft side wall 20 as described below to have sufficient column strength and hoop strength for advancement through the incision in the patient's skin and blood vessel and through the tortuous vasculature. It will be understood that proximal catheter shaft 30 can be constructed in other ways than specifically described below to achieve this end. However, the construction of proximal catheter shaft 30 makes it relatively stiff and capable of perforating a blood vessel wall if the catheter shaft distal end is aimed against it and advanced. The distal soft tip 40 that is attached to its distal end is intended to offset that capability.

Figure 3:
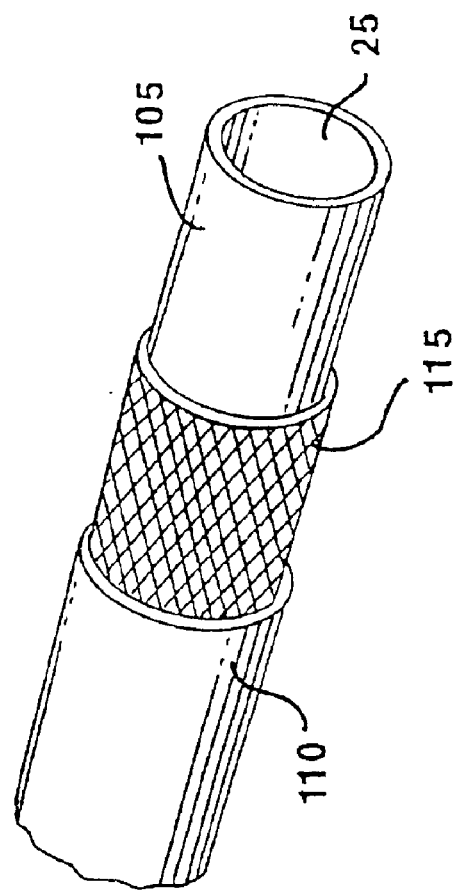
FIG. 3 is a perspective view of a section of the relatively stiff catheter shaft peeled back to reveal an inner tubular sheath, an outer tubular sheath and a wire braid tube sandwiched between the inner and outer tubular sheaths.
Figure 2:
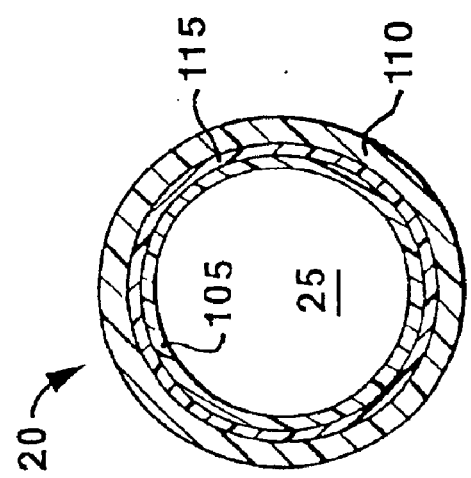
FIG. 2 is an enlarged cross-section view of the relatively stiff catheter shaft take along lines 2—2 in FIG. 1.

A preferred embodiment of the construction of the catheter shaft side wall of the catheter shaft 30 is depicted in FIGS. 2 and 3. The catheter shaft side wall 20 is preferably formed in the manner taught in the commonly assigned above-referenced '910 patent and '682 patent application. In accordance with this preferred embodiment of the invention, at least the proximal catheter shaft 30 is formed of an outer tubular sheath 110, an inner tubular sheath 105, and a wire braid tube 115 embedded in a polymer and sandwiched between the outer and inner tubular sheathes 110 and 105.

Typically, the inner tubular sheath 105 is formed from a single material, preferably a lubricious polymer, such as a fluorocarbon (e.g., polytetrafluoroethylene (PTFE), a polyamide (e.g. nylon), polyester block amides (PEBA), a polyolefin, a polyimide, or the like. It would also be possible to form the inner tubular sheath 105 as a laminate structure comprising a non-lubricious outer layer and an inner lumen surrounding a layer or coating of a more lubricious material. In one preferred embodiment, the inner sheath 105 is extruded of Shore 70D PEBAX® polyether block-amide copolymer, and its side wall is about 0.03 mm to 0.08 mm thick.

The wire braid tube 115 comprises "warp" and "weft" wire filaments braided in a fabric basket weave pattern wound to form a tube. The wire braid tube 115 may be woven directly over the inner tubular sheath 105 using conventional fabric weaving techniques. Or, the wire braid tube 115 may be woven over a mandrel using conventional braiding techniques and then fitted over the inner tubular sheath 105. The wire filaments have a very small cross-sectional area while possessing sufficient tensile strength to undergo the braiding process. Preferably, flat wire filaments of stainless steel, a shape memory alloy (e.g., Nitinol), polymeric fibers, or the like, are used. Stainless steel filaments having a flat cross-section with a thickness of 0.076 mm are particularly preferred.

The outer tubular sheath 110 is then injection molded over the wire braid tube 115 after the wire braid tube 115 is fitted or formed over the inner tubular sheath 105. The outer tubular sheath 110 can be formed of a variety of materials and is preferably composed of a thermoplastic material having a hardness in the range from Shore 30A to Shore 74D. Exemplary materials include polyamide, polyether block amides (PEBAX® or VESTAMID®), polyurethanes, silicone rubbers, nylons, polyethylenes, fluorinated hydrocarbon polymers, and the like. In the preferred embodiment, the outer sheath 110 is injection molded of either Shore 70D PEBAX® polyether block-polyamide, or Shore 74D VESTAMID® polyether block-polyamide.

In one preferred embodiment, a 6 F proximal catheter shaft 30 is constructed in this manner having an outer diameter of about 2.03 mm to 2.06 mm and a catheter lumen inner diameter of about 1.70 mm to 1.72 mm. The resulting composite side wall thickness is about 0.165 mm to 0.180 mm. Such a catheter shaft 30 has a hoop strength or crush resistance to a load of 2–7 pounds applied perpendicular to its longitudinal axis. The catheter body also exhibits an elastic modulus of between 28,000 psi and 40,000 psi under standard axial load conditions. The catheter body formed of the outer, inner and wire braid intermediate sheaths also has a kink resistance which enables it to withstand a load of 0.5 pounds moment weight for a minimum deflection of 30° before the side wall kinks.

In the preferred embodiment, the distal end 35 of the catheter shaft 30 is coupled directly with the proximal end of the distal soft tip 40 along an attachment junction 55, wherein the adhesion is effected using a tubular sleeve 120 overlying and filling the attachment junction in a manner described in reference to FIGS. 4–10. The distal soft tip 40 is tubular and has a side wall that surrounds a soft tip lumen that is the distal part of the catheter body lumen 25 and terminates at the distal lumen end opening 45. The distal soft tip 40 will generally be relatively short, typically having a length in the range from about 1.0 mm to 3.0 cm. Preferably, the distal soft tip 40 extends about 3.5 mm +/–0.50 mm distally from the distal end of the sleeve 120 and extends proximally within the sleeve 120 sufficiently so that its proximal end is within the sleeve 120. The side wall of the distal soft tip 40 is flexible enough that the side wall can buckle slightly when it bears against a blood vessel side wall and will not perforate the blood vessel side wall.

In this embodiment where a transition segment is not employed, the selection of polymer materials for the distal soft tip 40 in relation to the polymer materials of the catheter shaft outer tubular sheath 110 is also based upon considerations of flexural modulus and tensile strength. As noted above, the tensile strength must be sufficient to ensure an 18N minimum bond strength between the distal soft tip 40 and the outer tubular sheath 110 in the attachment junction. Polymer materials should be chosen for the distal soft tip 40 with a tensile strength ratio of greater than 1.25 and flexural modulus ratio of less than 15.0. The result of the material selections and the modified surface geometry of the catheter shaft distal end 35 and the proximal, mating end of the distal soft tip 40 is a bond in the attachment junction 55 in excess of 18N. For a catheter wall thickness of less than 0.3 mm, a polymer exhibiting a minimum tensile strength of 30 MPa is required for the distal soft tip 30. These criteria are met with a material such as Shore 55D PEBAX® polyether block-amide copolymer, without any reinforcing material added. The distal soft tip can be comprised of such a polyether-polyamide material having a Shore durometer of about 40D–55D.

The distal soft tip 40 is preferably pre-formed having an inner lumen, side wall thickness and outer diameter that matches the like dimensions of the catheter shaft 30 (or any intermediate transition segment). In accordance with the above referenced '241 application, one or more radiopaque stripes can be co-extruded with the extrusion of the tubular side wall of the tubing from which the distal soft tip 40 is cut.

Figure 4:
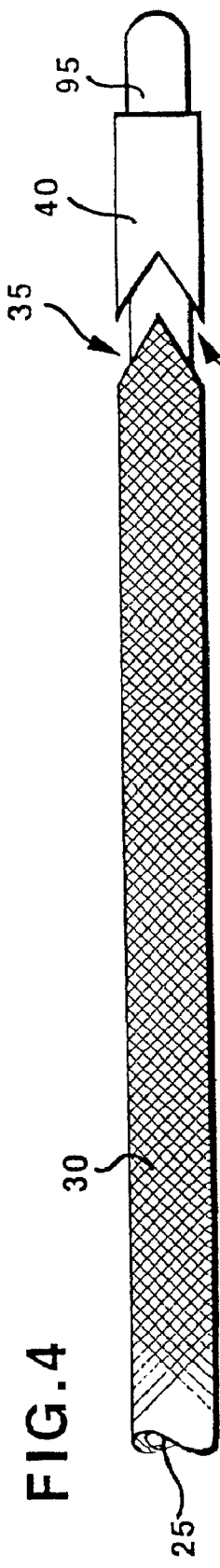
FIGS. 4 through 8 are plan views of the steps of a preferred method of attaching the distal soft tip to the catheter shaft distal end along the attachment junction employing molding a sleeve of thermoplastic material over the attachment junction.

FIGS. 4–8 show the sequential attachment steps of the method of the present invention. FIG. 4 depicts the distal soft tip 40 slipped over a mandrel 95 to be aligned with and attached to the catheter shaft 30 that is also shown positioned over the mandrel 95. In this illustrated embodiment, the proximal end 125 of the distal soft tip 40 and the distal end 35 of the catheter shaft 30 have been cut to each have two complementary, V-shaped, ungular cut sections of the type that are described in detail in the above-referenced '910 patent and also described in the above-referenced '241 patent application. The manner of making the ungular cuts is also described in the above-referenced '910 patent and in the above-referenced '241 patent application. The term "ungular" is derived from the expression "ungula of a right circular cylinder" as defined and illustrated in the *Standard Handbook for Mechanical Engineers,* Theodore Baumeister, ed., McGraw-Hill Book Co., NY, N.Y., pp. 2–19–20. However, the method of the present invention can also be employed with other complementary shaped mating catheter shaft distal ends and soft tip proximal ends for effecting a butt joint thereof so that the inner lumen diameter of the catheter body is constant through its length.

Figure 5:
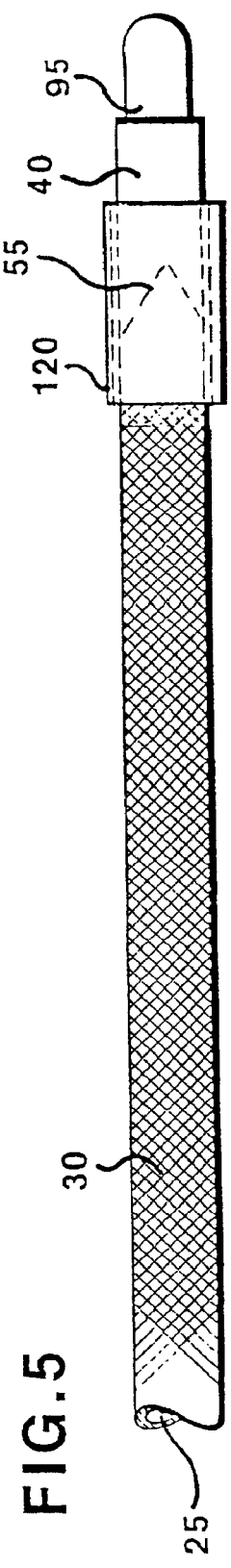

In FIG. 4, the distal soft tip and the catheter shaft 30 are assembled prior to bonding by first inserting a TEFLON® coated stainless steel mandrel 95 into the catheter lumen 25 to a depth of approximately 10.0 cm with approximately 5.0 cm extending distal to the catheter shaft distal end 35. The stainless steel mandrel 95 is sized to a sliding fit within catheter shaft lumen 25 and provides rigidity and maintains concentricity for subsequent bonding of the catheter shaft distal end 35 to the soft tip proximal end 125 at the attachment junction 55. The distal soft tip 40 is advanced over the distal end of the stainless steel mandrel 95 and rotated to align the complementary ungular cut sections of the catheter shaft distal end 35 and the soft tip proximal end 125 in an interlocking, mating manner along the attachment junction 55 as shown in FIG. 5. There are interstitial spaces between the complementary ungular cut sections of the catheter shaft distal end 35 and the soft tip proximal end 125 along the length of the attachment junction 55 due to the irregular points of contact arising from the manner of making the cuts.

At this point, components depicted in FIG. 4 are subjected to localized heating about the complementary ungular cut sections of the catheter shaft distal end 35 and the soft tip proximal end 125, e.g., by application of RF energy. A sub-assembly of the catheter shaft 30 and the distal soft tip 40 is formed as the materials of the abutting ends melt together. In this process, the reinforcing wire braid tube 115 just proximal to the junction 55 can become exposed due to melting and shrinkage of the catheter shaft outer tubular sheath 120.

In FIG. 5, the sleeve 120 is slipped over the catheter shaft 30 and the distal soft tip 40 so that it overlies and covers the attachment junction 55. The sleeve 120 is preferably formed of a tube of Shore 40D PEBAX® polyether block-amide copolymer, without any reinforcing material added. The sleeve 120 can be comprised of a polyether-polyamide material having a Shore durometer of about 40D–55D. The sleeve 120 preferably has a tube wall thickness of 0.76 mm and a 5.0 mm length. The inner diameter of sleeve 120 is selected to be just sufficiently larger than the catheter body outer diameter to allow it to be slid over the distal soft tip 40 and the catheter shaft 30 to the position shown in FIG. 5.

Figure 6:
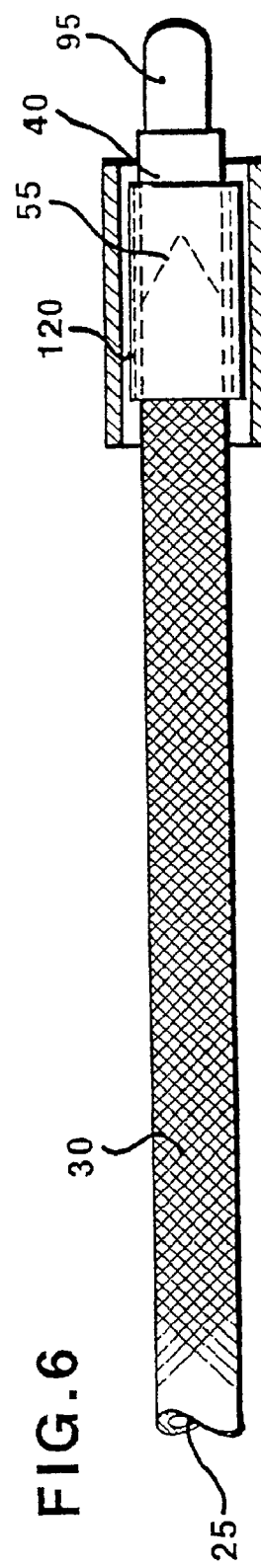
Figure 7:
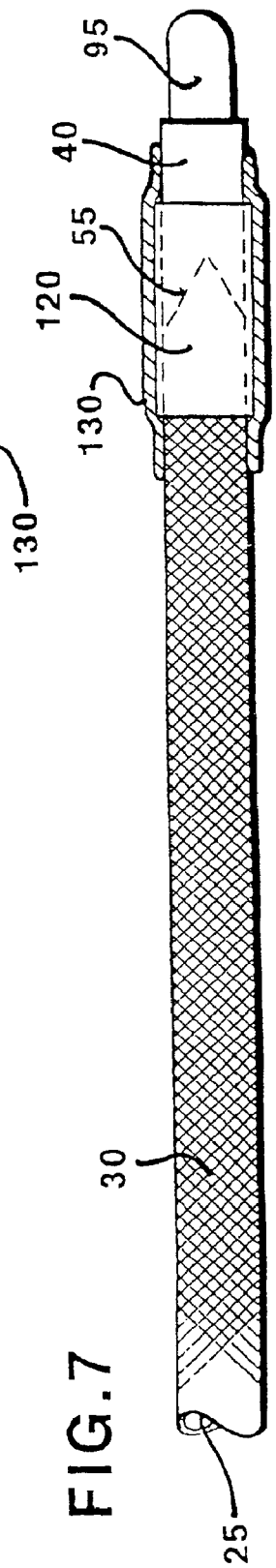

After the sleeve 120 is positioned as shown in FIG. 5, a further heat shrink tube 130 (shown in cross-section in FIGS. 6–8) is fitted over the sleeve 120 as shown in FIG. 6. The heat shrink tube extends proximally a distance of about 50 mm from the proximal end of the sleeve 120 and distally about 13.5 mm distal to the distal end of the sleeve 120 and over the mandrel 95. The assembly of FIG. 6 is then subjected to heat to effect the shrinkage of the heat shrink tube 130 tightly against the sleeve 120 and portions of the distal soft tip 40 and the catheter shaft 30 as shown in FIG. 7. The heat continues to be applied for a sufficient time to cause the sleeve 120 and the underlying distal soft tip 40 and the catheter shaft outer and inner layers 110 and 105 to partially melt so that the plastic material flows into and fills the interstitial spaces between the complementary ungular cut sections of the catheter shaft distal end 35 and the soft tip proximal end 125 along the length of the attachment junction 55. The heat shrink tube 130 is preferably formed of Teflon FEP (fluorinated ethylene propylene) which does not melt and mix with these catheter body and sleeve materials. The shrinkage of the heat shrink tube 130 applies compressive force to the thin walled sleeve 120 and forces it against the surfaces of the distal soft tip 40 and the catheter body 30. The sleeve 120 is compressed from its starting wall thickness of about 0.76 mm to a resulting thin film thickness of about 0.38 mm that only slightly increases the outer diameter of the catheter body.

Figure 8:
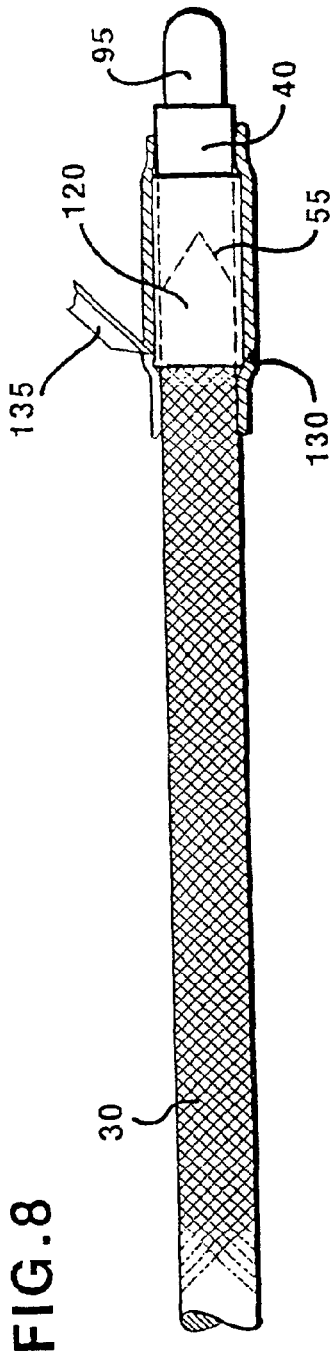
Figure 9:
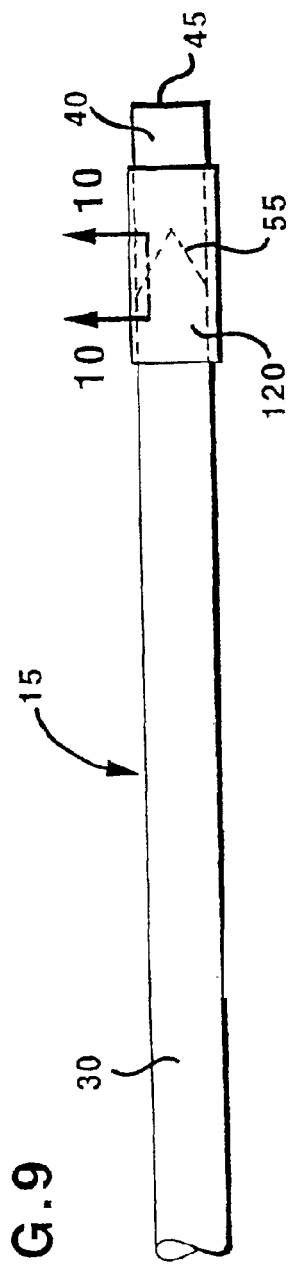
FIG. 9 is a plan view of the sleeve overlying the attachment junction.

In FIG. 8, the heat shrink tube 130 is cut using a blade 135 along its length taking care to avoid cutting the underlying sleeve 120 revealing the resulting catheter body 15 shown in FIG. 9. In FIG. 9, the thickness of sleeve 120 is exaggerated from what is actually realized using this process with the materials, and sleeve wall thickness described above. In practice, the tubular sleeve has an outer diameter of 2.108 mm to 2.159 mm, which is only slightly greater than the catheter shaft and the distal soft tip outer diameters. The thickness of sleeve 120 is barely perceptible to touch or sight, and the presence of the sleeve 120 can only be observed because it is tinted to have a different color than the colors of the catheter shaft 30 and the distal soft tip for identification.

Figure 10:
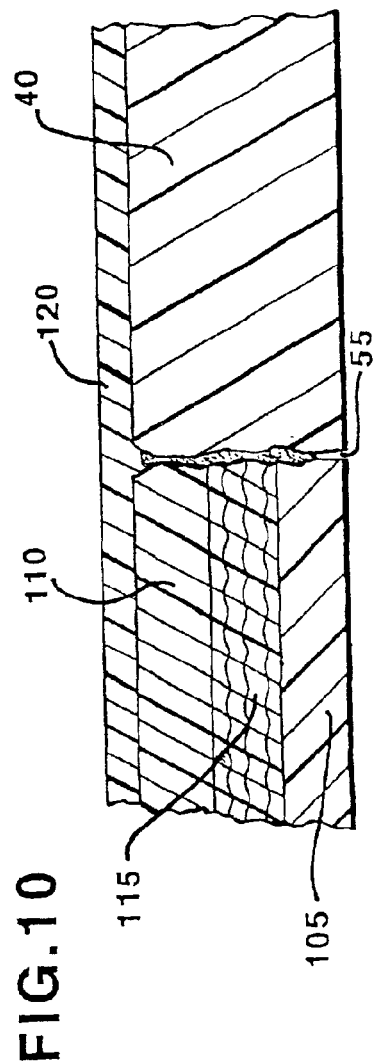
FIG. 10 is an enlarged cross-section view of the resulting catheter wall along the section lines 10—10 in FIG. 9.

The composite catheter body wall at the attachment junction 55 is shown in FIG. 10. A melt zone is formed along the attachment junction 55 that fills any interstitial spaces caused by the irregular points of mutual contact of the catheter shaft distal end 35 and the soft tip proximal end 125 (shown in FIG. 4). The material of the melt zone comprises the material of the sleeve 120 and the materials of the distal soft tip 40 and the outer and inner catheter shaft layers 110 and 105.

The modified surface geometry of the soft tip proximal end 125 and the catheter shaft distal end 35 increases the butt weld zone adhesion surface area and decreases stress concentration along the butt weld zone 55. The use of the interlocking ungular sections results in a surface area 200% greater than the surface area of a simple butt joint. Further, the surface area of the catheter shaft distal end 35 is between 110–200% that of a frusto-conical joint. Also, stress concentration which is exhibited by the junctions of the flexible tubular elements is reduced on the catheter shaft 30 because the oblique planes which define the attachment junction 55 between the catheter shaft 30 and the distal soft tip 40 are not perpendicular to the tensile and flexural loads which are applied to the distal soft tip 40 during use.

In a three (or more) segment embodiment of the catheter body 15, a transition segment is located immediately distally of catheter shaft distal end at attachment junction at a location spaced within 30 cm of the catheter body distal end 50, usually from 1 cm to 10 cm of the catheter body distal end 50. In this embodiment, the distal soft tip 40 extends distally from the distal end of the transition segment. The transition segment has an intermediate level reinforcement providing an intermediate level of stiffness, column strength, and hoop strength between the high levels of the catheter shaft 30 and the low levels of the distal soft tip 40. Consequently, the transition segment has an intermediate level of side wall flexibility between the low level of flexibility of the catheter shaft 30 and the high level of flexibility of the distal soft tip 40.

When the transition segment is used, the selection of materials for the transition segment is based upon considerations of tensile strength, processing temperature compatibility with the polymers comprising the catheter shaft 30, and flexural modulus. The materials are selected to result in a minimum tensile strength that depends on the outer diameter and wall thickness of the catheter body.

When the intermediate or transition segment is employed, the sleeve 120 is elongated to extend over it and over a distal portion of the catheter shaft 30 and a proximal portion of the distal soft tip as described above with respect to the preferred embodiment. Alternatively, an additional separate sleeve like sleeve 120 can be positioned to bridge the additional attachment junction of the abutting distal and proximal ends of the catheter shaft 30 and the transition segment. The same technique can be followed for any number of intermediate segments. In all such cases, the method steps of FIGS. 4–8 are followed to minimize the thickness of the sleeve 120 and provide strong adhesion between it and the underlying catheter shaft portion and segment portion outer walls adjoining each attachment junction.

In all such cases, a strong bond can be formed at each abutting attachment junction if the polymer materials of the catheter shaft, any intermediate segment(s) and the distal soft tip are chosen to have melt compatibility within a common temperature range. The above specified VESTAMID and PEBAX® polyether block-amide copolymer tube materials having the differing Shore hardnesses have compatible melt temperatures and adhere well to one another.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. The method of fabricating a catheter body comprising the steps of:

providing a tubular catheter shaft including a catheter shaft proximal end and a catheter shaft distal end, the catheter shaft having a catheter shaft outer diameter and enclosing at least one catheter shaft lumen;

providing a tubular distal catheter segment including a segment proximal end and a segment distal end, the distal segment having a segment outer diameter substantially the same as the catheter shaft outer diameter and a segment lumen extending between the segment proximal end and the segment distal end;

aligning the segment lumen and the segment outer diameter with the catheter shaft lumen and the catheter shaft outer diameter, respectively, to form an attachment junction; and melt bonding a tubular sleeve to a distal portion of the catheter shaft and a proximal portion of the distal segment bridging the attachment junction such that at least part of the attachment junction comprises melted material from each of the tubular sleeve, the catheter shaft, and the distal segment.

2. The method of claim 1 wherein the attachment junction is characterized by interstitial spaces caused by irregular contact of the segment proximal end with the catheter shaft distal end, and wherein the bonding step further comprises the steps of:

heating the attachment junction to effect a bond between the segment proximal end with the catheter shaft distal end;

fitting the tubular sleeve over a distal portion of the catheter shaft and a proximal portion of the distal segment bridging the attachment junction;

applying heat and pressure to the tubular sleeve and the underlying distal portion of the catheter shaft and proximal portion of the distal segment bridging the attachment junction to further melt and force the materials of the tubular sleeve and the catheter shaft and the distal segment together to fill the interstitial spaces of the attachment junction and to reduce the outer diameter of the sleeve.

3. The method of claim 2, wherein the step of applying heat and pressure further comprises the steps of fitting a heat shrink tube over the tubular sleeve and applying heat sufficient to shrink the heat shrink tube over and apply force to the assembly of the tubular sleeve overlying the distal portion of the catheter shaft and the proximal portion of the distal segment bridging the attachment junction and to melt and force the materials of the tubular sleeve and the catheter shaft and the distal-segment together to fill the interstitial spaces of the attachment junction, the shrinkage of the heat shrink tube reducing the outer diameter of the sleeve, and removing the heat shrink tube from the assembly.

4. The method of claim 3, further comprising the step of:

forming the catheter shaft distal end and the segment proximal end with a like plurality of ungular cut sections that are complementary in shape to one another, and wherein the aligning step further comprises the step of:

aligning and mating the ungular cut sections of the segment proximal end with the ungular cut sections of the catheter shaft distal end along the attachment junction.

5. The method of claim 3, further comprising the step of:

forming the catheter shaft distal end and the segment proximal end with a like plurality of ungular cut sections that are complementary in shape to one another; and wherein the aligning step further comprises the step of:

aligning and mating the ungular cut sections of the segment proximal end with the ungular cut sections of the catheter shaft distal end along the attachment junction.

6. The method of claim 1, wherein the distal catheter segment comprises a distal soft tip for providing an atraumatic distal tip of the catheter body.

* * * * *